(12) United States Patent
Johann et al.

(10) Patent No.: US 9,750,251 B2
(45) Date of Patent: Sep. 5, 2017

(54) LIQUID HERBICIDAL PREPARATIONS

(75) Inventors: Gerhard Johann, Burscheid (DE); Udo Bickers, Kelkheim (DE); Mandy Denner, Hochheim-Massenheim (DE); Rainer Buckpesch, Hofheim (DE); Frank Sixl, Rechtsupweg (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 233 days.

(21) Appl. No.: 12/867,618

(22) PCT Filed: Feb. 5, 2009

(86) PCT No.: PCT/EP2009/000766
§ 371 (c)(1),
(2), (4) Date: Aug. 13, 2010

(87) PCT Pub. No.: WO2009/100846
PCT Pub. Date: Aug. 20, 2009

(65) Prior Publication Data
US 2010/0331184 A1  Dec. 30, 2010

(30) Foreign Application Priority Data
Feb. 14, 2008  (EP) .................................. 08002708

(51) Int. Cl.
| A01N 43/54 | (2006.01) |
| A01N 43/12 | (2006.01) |
| A01N 47/22 | (2006.01) |
| A01N 25/02 | (2006.01) |
| A01N 25/04 | (2006.01) |
| A01N 25/30 | (2006.01) |

(52) U.S. Cl.
CPC ............ *A01N 43/54* (2013.01); *A01N 25/02* (2013.01); *A01N 25/04* (2013.01); *A01N 25/30* (2013.01); *A01N 43/12* (2013.01); *A01N 47/22* (2013.01)

(58) Field of Classification Search
CPC ........ A01N 43/54; A01N 43/12; A01N 47/22; A01N 25/04; A01N 25/30; A01N 25/02
USPC ........................................................ 504/136
See application file for complete search history.

(56) References Cited

U.S. PATENT DOCUMENTS

| 3,933,460 A * | 1/1976 | Fischer .................... 504/137 |
| 6,627,595 B2 * | 9/2003 | Wurtz et al. .................. 510/422 |
| 2005/0221993 A1 | 10/2005 | Long |
| 2006/0142163 A1 * | 6/2006 | Wurtz et al. .................. 504/364 |

FOREIGN PATENT DOCUMENTS

| DE | 2334787 | 2/1975 |
| DE | 19913036 | 9/2000 |
| JP | H-06-510767 | 12/1994 |
| JP | H-07501789 A | 2/1995 |
| JP | H-09-500892 A | 1/1997 |
| WO | 9304585 A1 | 3/1993 |
| WO | 93-05652 A1 | 4/1993 |
| WO | 9503697 A1 | 2/1995 |
| WO | WO 01/47356 | 7/2001 |

OTHER PUBLICATIONS

Clayton Lenacil 80W. Safety Data Sheet [online]. Clayton Plant Protection, 2004, [retrieved on Sep. 4, 2012]. Retrieved from the Internet:<http://www.lookchem.com/msds/%5c2008-11%5c812bdc2a-6ca3-49bf-9390-80592e175c79.pdf> 2 pages.*
Cioni et al. "Weed Control in Sugarbeet", Sugar Tech (2010), vol. 12 No. 3-4, pp. 243-255.
Fisher, S J et al. "Post-emergence broad-leaved weed control in sugar beet with triflusulfuron in the UK 1993-1994" Brighton Crop Protection Conference. Weeds, British Crop Protection Council, S.L., GB, vol. 3, Jan. 1, 1995, pp. 853-858.
Lainsbury, M.A. et al. "Sugar beet weed control using simple herbicide mixtures: Can improvements to the current 'FAR' system be achieved?" Conference Proceedings BCPC Conference, Weeds, vol. 1-2, Dec. 11, 2001, pp. 237-242.

* cited by examiner

*Primary Examiner* — John Pak
*Assistant Examiner* — Andriae M Holt
(74) *Attorney, Agent, or Firm* — McBee Moore Woodward Vanik IP; Susan McBee; David Woodward

(57) ABSTRACT

Herbicidal oil dispersions comprising
(a) desmedipham and/or phenmedipham, ethofumesate and lenacil,
(b) one or more surfactants,
c) one or more compounds which as far as possible are polar but at the same time are water-insoluble or have a solubility in water of up to 5 g/l, from the group of fully esterified organic phosphates and fully esterified phosphonates, as solvents,
d) optionally further organic solvents,
e) optionally further, customary formulating auxiliaries,
f) optionally water
are stable formulations and are suitable for controlling weeds, particularly for selective control in beet crops.

11 Claims, No Drawings

LIQUID HERBICIDAL PREPARATIONS

The invention pertains to the technical field of preparations (formulations) of crop protectant active ingredients, more particularly to the field of coformulations, i.e., the provision of two or more crop protectant active ingredients in one formulation. Specifically, the invention pertains to liquid coformulations of crop protectants for control of weeds in dicotyledonous crops, such as beet crops, preferably sugar beet crops.

For weed control in beet crops, structurally different single active ingredients are approved. For optimized application, one or more of these active ingredients are often used in combination, in order to allow the properties of the single active ingredients to be exploited in unison in one application (expansion of the weed spectrum, closing of activity gaps) or else because the single active ingredients are synergistic in combination, i.e., produce advantageous superadditive activity boosts. The joint application of active ingredients has diverse technical aspects, of course, depending on whether the active ingredients are to be combined only in a tank mix or are to be actually provided in the form of a storable completed mixture.

First of all, single active ingredients or active ingredient mixtures are generally employed not as the compounds alone but instead, depending on field of application and desired physical application form, in combination with certain auxiliaries—that is, they are "formulated". Active crop protectant ingredients can be formulated in a variety of ways, according to the prevailing biological and/or physicochemical parameters. Generally speaking, the following formulation options will be contemplated: wettable powders (WP), oil-in-water or water-in-oil emulsions (EW or EO), suspensions (SC), suspoemulsions (SE), emulsifiable concentrates (EC) or else granules for soil application or broadcast application, or water-dispersible granules (WG). The stated types of formulation are known in principle and are described for example in Winnacker-Küchler, "Chemische Technologie", volume 7, C. Hanser-Verlag, Munich, $4^{th}$ edition 1986; van Valkenburg, "Pesticide Formulations", Marcel-Dekker N.Y., 1973; K. Martens, "Spray Drying Handbook", 3rd Ed., 1979, G. Goodwin Ltd. London.

Where the active ingredients to be formulated are of low polarity, examples being compounds which are not saltlike or which contain predominantly hydrophobic radicals and are therefore virtually insoluble in water, the formulating options are of course limited. This applies, for example, to active herbicidal ingredients such as desmedipham (DMP) and phenmedipham (PMP), which belong to the group of the biscarbamates and whose solubility in water is 7 mg/l at 20° C. and 4.7 mg/l at room temperature, respectively. The situation with active herbicidal ingredients from the benzofuranyl sulfonates group, such as ethofumesate (water solubility: 50 mg/l at 25° C.) or benfuresate (water solubility: 261 mg/l at 25° C.) is similar. Another known active ingredient used for weed control in beet crops is lenacil, an active ingredient from the structural class of the uracils (i.e., pyrimidinediones). It is additionally known that lenacil can be combined with other active crop protectant ingredients such as phenmedipham or ethofumesate, as for example in tank mixes or some ready-to-use formulations; see, for example, "The Pesticide Manual", British Crop Protection Council, $14^{th}$ edition 2006. Lenacil as well, at 3 mg/l at 25° C., has a comparatively low water solubility.

Liquid formulations of certain herbicides of the type set out above are already known. Thus, for example, WO-A-85/01286 describes liquid formulations containing PMP and/or metamitron. Solvents referred to in this context include esters of polyalcohols, ethers, ketones, water-insoluble alcohols, (poly)glycols, and oils of both vegetable and mineral origin, while suitable emulsifiers specified for the liquid formulations described include, generally, non-ionic, but also ampholytic, cationic or anionic surfactants.

Alternative options to solvent-based emulsifiable concentrates for the active ingredients identified above include water-containing suspension concentrates (SC) and suspoemulsions (SE). Formulations of this kind are described in WO-A-95/23505, EP-A-0637910, and WO-A-92/09195.

EP1164842 and EP1251736 have already disclosed surfactant-solvent systems which allow the production of stable liquid formulations, such as emulsifiable concentrates or suspension concentrates, for coformulations of the active ingredients desmedipham (DMP) and phenmedipham (PMP) and ethofumesate. These coformulations are suitable for the control of weeds in beet crops.

The greater the number of structurally different active ingredients to be combined in a formulation, the greater the restrictions on formulation freedom that apply. Alternatively, a storable ready-to-mixture generally offers the advantage over a tank mix that the active ingredients and formulating auxiliaries are present in proportions tailored to one another, whereas with a tank mix the proportions must be set by the user each time and, depending on the formulations used for the individual components, there may be incompatibilities among the auxiliaries.

In addition to the purely formulation-related object of providing a stable concentrated formulation which when diluted with water produces spray liquors having properties that are advantageous from a physical/applications standpoint, a preferred additional object is that of providing formulations having biologically advantageous properties. The auxiliaries to be used for the formulations ought to have broad suitability for use and ought to support, and as far as possible not adversely affect, the biological properties of the active ingredients used.

It is known that in certain cases the biological activity of some active pesticidal ingredients may be boosted by organic compounds of low molecular mass. For instance, according to BE-A-597284, full or partial esters based on ortho-phosphoric acid and alkyl-, aryl-, alkylaryl-, cycloalkyl- and/or heterocycle-based alcohols are suitable for boosting the activity of herbicides, such as of herbicidal phenylurea derivatives such as monuron, azoles such as amitrole, triazines such as simazine, and propionic acid derivates such as dalapon. The phosphoric esters described specifically as auxiliaries in this context comprise relatively apolar or entirely water-soluble phosphoric esters, which are not particularly suitable for producing liquid concentrates. Nor does that specification mention the beet herbicides which are preferred in the context of the stated objected, such as biscarbamates (phen- and desmedipham) or benzofuranyl sulfonates (ethofumesate).

DE-A-2914164 describes synergistic effects arising with herbicides with a desiccative effect on crop plants, i.e., for example, herbicides from the group of the phenylureas (e.g., metoxuron, diuron) or the triazines (e.g., atrazine, simazine), when combined with solvents of the kind used in the metallurgical industry, in metal recovery or as plasticizers for polymers. The publication does not reveal which of the solvents cited in general terms are suitable for producing liquid concentrates and liquid preparations preparable therefrom.

DE-A-2334787 has already described synergistic herbicidal mixtures for use in sugar beet crops. Activities are described inter alia for combinations of the active ingredients ethofumesate, phenmedipham, and lenacil (see example 18), applied in the form of a dispersion. The publication does not reveal the composition of the dispersion, and nor does it reveal whether the formulation has a particular effect on the biological results. Furthermore, information as to which formulations are particularly suitable for the coformulations is absent.

The object was therefore to provide stable, ready-to-use formulations particularly suitable for weed control in beet crops.

It has now been surprisingly found that certain surfactant-solvent systems are especially suitable for use for the coformulation of active ingredients from the group of biscarbamate herbicides, such as phenmedipham and/or desmedipham, of benzofuranyl sulfonates, such as ethofumesate, and lenacil.

The invention provides herbicidal oil dispersions which comprise
(a) one or more biscarbamate herbicides of the formulae (a1) and (a2),

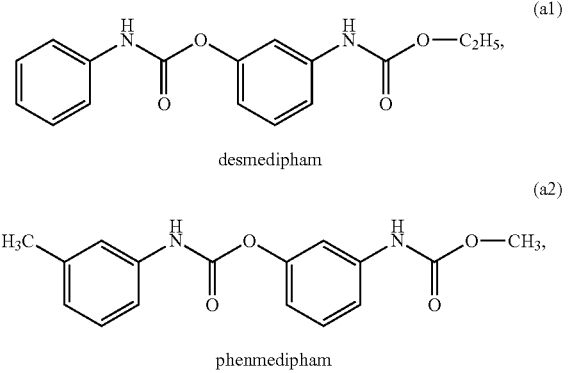

one or more benzofuransulfonate herbicides, such as ethofumesate (a3), and lenacil (a4) of the formula

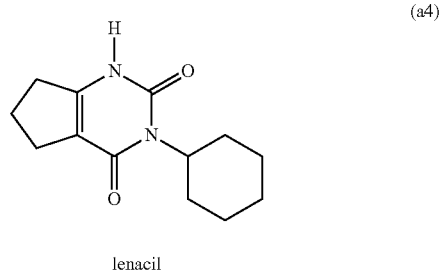 [SMILES: O=c1[nH]c2c(c(=O)n1C1CCCCC1)CCC2]

(b) one or more surfactants,
(c) one or more compounds which as far as possible are polar, but at the same time are water-insoluble or have a solubility in water of up to 5 g/l, preferably up to 3 g/l, more particularly up to 2 g/l, from the group of fully esterified organic phosphates and fully esterified phosphonates, as solvents,
(d) if desired, other organic solvents,
(e) if desired, other, customary formulating auxiliaries,
(f) if desired, water.

The compounds of the formulae (a1) and (a2) are derivatives of carbamic acid. The herbicidal properties of these compounds are described in DE-A-3799758, for example. The compound of the formula (a1) with the common name "desmedipham" has the chemical name ethyl 3-(phenylcarbamoyloxy)phenylcarbamate, and the compound of the formula (a2) with the common name "phenmedipham" has the chemical name methyl 3-(3-methylphenylcarbamoyloxy)phenylcarbamate. The compound of the formula (a3) with the common name "ethofumesate" has the chemical name (2RS)-2,3-dihydro-3,3-dimethylbenzofuran-5-yl ethanesulfonate. Ethofumesate contains an asymmetric carbon atom. Both enantiomers of ethofumesate are considered to be biologically active. The formula (a3) therefore encompasses all stereoisomers and mixtures thereof, more particularly the racemate. Their herbicidal properties are described in GB-A-1271659, for example. The compound of the formula (a4) with the common name "lenacil" has the chemical name 3-cyclohexyl-1,5,6,7-tetrahydrocyclopentapyrimidine-2,4 (3H)-dione. Herbicidal properties of lenacil are described in U.S. Pat. No. 3,235,360, for example.

The active ingredients (a1) to (a4) are also described in "The Pesticide Manual", British Crop Protection Council, 14$^{th}$ edition, 2006, and literature cited therein. They are known for use as beet herbicides.

Surfactants (b) which can be employed in accordance with the invention may comprise one or more surfactants based on carbocyclic aromatics ("aromatic-based" for short) (b1) or on a nonaromatic basis (b2), or a mixture of surfactants on an aromatic basis and on a nonaromatic basis (b1) and (b2).

Aromatic-based surfactants (b1) are, for example, surface-active benzenes or phenols, substituted by one or more alkyl groups and subsequently derivatized, which are soluble in the solvent phase and which emulsify this phase—together with the active ingredients dissolved therein—on dilution with water (to form the spray liquor). Examples of surfactants of this kind are as follows:

(b1.1) phenols, phenyl ($C_1$-$C_4$)alkyl ethers or (poly)alkoxylated phenols [=phenol (poly)alkylene glycol ethers], for example with 1 to 50 alkyleneoxy units in the (poly)alkyleneoxy moiety, the alkylene moiety having preferably 1 to 4 carbon atoms in each case, preferably phenol reacted with 3 to 10 mol of alkylene oxide, (b1.2) (poly)alkylphenols or (poly)alkylphenol alkoxylates [=polyalkylphenol (poly)alkylene glycol ethers], for example with 1 to 12 carbon atoms per alkyl radical and 1 to 150 alkyleneoxy units in the polyalkyleneoxy moiety, preferably tri-n-butylphenol, triisobutylphenol or tri(sec-butyl)phenol reacted with 1 to 50 mol of ethylene oxide, (b1.3) polyarylphenols or polyarylphenol alkoxylates [=polyarylphenol (poly)alkylene glycol ethers], for example tristyrylphenol polyalkylene glycol ethers having 1 to 150 alkyleneoxy units in the polyalkyleneoxy moiety, preferably tristyrylphenol reacted with 1 to 50 mol of ethylene oxide, (b1.4) compounds which formally represent the reaction product of the molecules described under (b1.1) to (b1.3) with sulfuric acid or phosphoric acid, and their salts neutralized with suitable bases, examples being the acidic phosphoric ester of triply ethoxylated phenol, the acidic phosphoric ester of a nonylphenol reacted with 9 mol of ethylene oxide, and the phosphoric ester, neutralized with triethanolamine, of the reaction product of 20 mol of ethylene oxide and 1 mol of tristyrylphenol, and (b1.5) acidic (poly)alkyl- and (poly)aryl-benzenesulfonates and such neutralized with suitable bases, for example having 1 to 12 carbon atoms per alkyl radical and having up to 3 styrene units in the polyaryl radical, preferably (linear) dodecylbenzenesulfonic acid and the oil-soluble salts thereof, such as the isopropylammonium salt of dodecylbenzenesulfonic acid, for example.

With regard to the stated alkyleneoxy units, preference is given to 1,2-ethyleneoxy, 1,2-propyleneoxy, 1,2-butyleneoxy, 2,3-butylenoxy-, and 2,2-dimethyl-1,2-ethyleneoxy units, especially 1,2-ethyleneoxy units.

Preferred surfactants from the group of the aromatic-based surfactants are in particular, for example, phenol reacted with 4 to 10 mol of ethylene oxide, available commercially in the form of the Agrisol® products (Akcros) for example;

triisobutylphenol or tri(sec-butyl)phenol reacted with 4 to 50 mol of ethylene oxide, available commercially in the form of the Sapogenat T® products (Clariant), for example, e.g. Sapogenat T060 (ethoxylated tri(sec-butyl)phenol with 6 EO units or Sapogenat T080 (ethoxylated tri(sec-butyl) phenol with 8 EO units;

nonylphenol reacted with 4 to 50 mol of ethylene oxide, available commercially in the form of the Arkopal® products (Clariant), for example;

phosphated phenol ethoxylate (free acid), an example being ®Phospholan PHB14 (phosphated phenol ethoxylate with 4 EO units, Akzo);

tristyrylphenol reacted with 4 to 150 mol of ethylene oxide, an example being Soprophor CY/8® (Rhodia), and acidic (linear) dodecylbenzenesulfonate, available commercially in the form of the Marlon® products (Hüls), for example.

Surfactants (b2) on a nonaromatic basis, containing no carbocyclic aromatic structural moieties, are, for example, aliphatic-based, cycloaliphatic-based, olefin-based or heterocycle-based surfactants, examples being surface-active compounds having one or more alkyl groups, which are soluble in the solvent phase and are suitable for emulsifying that phase—together with active ingredients dissolved therein—on dilution with water (to form the spray liquor). The compounds do not contain any carbocyclic aromatic rings, but may include ring structures, cycloalkyl for example, saturated or partially unsaturated heterocyclyl groups, and also, possibly, heteroaromatic groups. Preferred nonaromatic surfactants are those without heteroaromatic groups.

Examples of surfactants (b) of this kind are listed below, in which EO=1,2-ethylene oxide units, PO=1,2-propylene oxide units, and BO=butylene oxide units, preferably EO, PO, and BO=2,3-butyleneoxy or 2,2-dimethyl-1,2-ethyleneoxy units:

(b2.1) fatty alcohols having 10 to 24 carbon atoms with 0 to 60 EO and/or 0 to 20 PO and/or 0 to 15 BO in any order. The terminal hydroxyl groups of these compounds may be end group-capped by an alkyl, cycloalkyl or acyl radical having 1 to 24 carbon atoms. Examples of such compounds are as follows:

Genapol® C, L, O, T, UD, UDD, and X products from Clariant, Plurafac® and Lutensol® A, AT, ON, and TO products from BASF, Marlipal® 24 and Marlipal® O13 products from Condea, Dehypon® products from Henkel, Ethylan® products from Akzo-Nobel such as Ethylan CD 120.

(b2.2) Anionic derivatives of the products described under (b2.1), in the form of ether carboxylates, sulfonates, sulfates, and phosphates, and their inorganic (e.g., alkali metal and alkaline earth metal) and organic (e.g., amine- or alkanolamine-based) salts, such as Genapol® LRO, Sandopan® products, Hostaphat/Hordaphos® products from Clariant, Servoxyl products from Elementis.

Copolymers consisting of EO, PO and/or BO units, such as, for example, block copolymers such as the Pluronic® products from BASF and the Synperonic® products from Uniquema with a molecular weight of 400 to $10^8$.

Alkylene oxide adducts of $C_1$-$C_9$ alcohols such as Atlox® 5000 from Uniquema or Hoe®-S3510 from Clariant.

Anionic derivatives of the products described under b2.3) and b2.4), in the form of ether carboxylates, sulfonates, sulfates, and phosphates, and their inorganic (e.g., alkali metal and alkaline earth metal) and organic (e.g., amine- or alkanolamine-based) salts.

(b2.3) Fatty acid alkoxylates and triglyceride alkoxylates such as the Serdox® NOG products from Condea, the Emulsogen® products from Clariant or the Alkamuls® OR products from Rhodia, salts of aliphatic, cycloaliphatic, and olefinic carboxylic acids and polycarboxylic acids, and also alpha-sulfo fatty acid esters as obtainable from Henkel.

(b2.4) Fatty acid amide alkoxylates such as the Comperlan® products from Henkel or the Amam® products from Rhodia.

Alkylene oxide adducts of alkynediols such as the Surfynol® products from Air Products. Sugar derivatives such as amino sugars and amido sugars from Clariant, glucitols from Clariant, alkylpolyglycosides in the form of the APG® products from Henkel or such as sorbitan esters in the form of the Span® or Tween® products from Uniquema or cyclodextrin esters or ethers from Wacker.

(b2.5) Surface-active cellulose derivatives and algin, pectin, and guar derivatives such as the Tylose® products from Clariant, the Manutex® products from Kelco, and guar derivatives from Cesalpina. Alkylene oxide adducts on a polyol basis, such as Polyglykol® products from Clariant. Interface-active polyglycerides and their derivatives from Clariant.

(b2.6) Sulfosuccinates, alkanesulfonates, paraffinsulfonates and olefinsulfonates such as Netzer IS®, Hoe® S1728, Hostapur® OS, Hostapur® SAS from Clariant, Triton® GR7ME and GR5 from Union Carbide, Empimin® products from Albright and Wilson, Marlon®-PS65 from Condea.

(b2.7) Sulfosuccinamates such as the Aerosol® products from Cytec or the Empimin® products from Albright and Wilson.

(b2.8) Alkylene oxide adducts of fatty amines, quaternary ammonium compounds having 8 to 22 carbon atoms ($C_8$-$C_{22}$), such as, for example, the Genamin® C, L, O, T products from Clariant.

(b2.9) Surface-active zwitterionic compounds such as taurides, betaines, and sulfobetaines, in the form of Tegotain® products from Goldschmidt, Hostapon® T and Arkopon® T products from Clariant.

(b2.10) Surface-active compounds on a silicone or silane basis, such as the Tegopren® products from Goldschmidt and the SE® products from Wacker, and also the Bevaloid®, Rhodorsil® and Silcolapse® products from Rhodia (Dow Corning, Reliance, GE, Bayer).

(b2.11) Perfluorinated or polyfluorinated surface-active compounds such as Fluowet® products from Clariant, the Bayowet® products from Bayer, the Zonyl® products from DuPont and products of this kind from Daikin and Asahi Glass.

(b2.12) Interface-active sulfonamides, e.g., from Bayer.

(b2.13) Interface-active polyacrylic and polymethacrylic derivatives such as the Sokalan® products from BASF.

(b2.14) Surface-active polyamides such as modified gelatins or derivatized polyaspartic acid from Bayer, and derivatives thereof.

(b2.15) Surfactant-type polyvinyl compounds such as modified PVP, such as the Luviskol® products from BASF and the Agrimer® products from ISP, or the derivatized polyvinyl acetates, such as the Mowilith® products from Clariant, or the polyvinyl butyrates, such as the Lutonal® products from BASF, the Vinnapas® and the Pioloform® products from Wacker, or modified polyvinyl alcohols such as the Mowiol® products from Clariant.

(b2.16) Surface-active polymers based on maleic anhydride and/or reaction products of maleic anhydride, and also copolymers comprising maleic anhydride and/or reaction products of maleic anhydride, such as the Agrimer® VEMA products from ISP.

(b2.17) Surface-active derivatives of montan, polyethylene, and polypropylene waxes, such as the Hoechst® waxes or the Licowet® products from Clariant.

(b2.18) Surface-active phosphonates and phosphinates such as Fluowet® PL from Clariant.

(b2.19) Polyhalogenated or perhalogenated surfactants such as, for example, Emulsogen® 1557 from Clariant.

The oil dispersions preferably comprise one or more aromatic-based surfactants (b1).

The oil dispersions of the invention may also comprise mixtures of the surfactants (b1) and (b2). Hence it is often advantageous, as well as nonionic surfactants (b1) and/or (b2), to use ionic surfactants, examples being anionic or cationic surfactants (b1) or (b2), respectively.

Preference is given, for example, to combinations of aromatic surfactants (b1) with anionic surfactants (b2), such as, for example, anionic surfactants from the group of the alkylpolyglycol ether carboxylates such as Akypo RLM 45® (Kao) or Marlowet 4538® (Condea).

Preference is also given, for example, to combinations of aromatic surfactants (b1) with nonionic and/or anionic surfactants (b2), such as, for example, nonionic surfactants from the group of the ethoxylated fats or fatty acids, examples being Emulsogen EL 400® (castor oil ethoxylate with 40 EO, Clariant), Etocas 12® (castor oil ethoxylate with 12 EO, Croda), Alkamuls OR/40 (castor oil ethoxylate with HLB of 14, Rhodia), Serdox NOG 600® (oleic acid ethoxylate with 14 to 15 EO, Servo), or else nonionic surfactant polymers based on alkylene oxide, such as, for example, ethylene oxide/propylene oxide block copolymers (e.g., Genapol PF40® (Clariant)), or anionic surfactants such as, for example, Servoxyl VPDZ 20/100 (phosphated, ethoxylated isotridecyl alcohol with 20 EO units, Elementis).

Organic phosphates and phosphonates [component (c), solvents] for the purposes of the invention are fully reacted, nonhydrolyzed esters of ortho-phosphoric acid or of an alkyl-, aryl-, alkylaryl-, poly(alkyl)-aryl- or poly(arylalkyl)-aryl-phosphonic acid. Those preferentially suitable are (as far as possible) polar compounds which at the same time, however, are largely insoluble in water, and which, on the basis of their interface activity, lower the interfacial tension of the oil droplets in the spray liquor that comprise the active ingredient (a) or the active ingredients (a), relative to the external aqueous phase, in such a way as to produce, in integration with the surfactants/emulsifiers that are additionally present in the formulation, a stable dilution/spray liquor which is impeccable from the standpoint of application technology. The limits for the stated water solubilities of component (c) are based on a measurement at 20° C. Of particularly preferential suitability are compounds of the aforementioned kind which before or after the esterification have been alkoxyated with ortho-phosphoric acid or phosphonic acid, more particularly tri(butoxyethyl) phosphate (TBEP), which possesses a water solubility of 1.1 g/l at 20° C.

The compounds of component (c) share the feature that in aqueous solution they do not form any aggregates that are micellar—detectable, for example, by light scattering measurements or other techniques. This distinguishes them from the phosphoric ester surfactants and justifies their classification as solvents.

Suitable polar and at the same time largely water-insoluble organic phosphoric esters [component (c)] are the esters of ortho-phosphoric acid that are formally reacted triply with alcohols, and the oxalkylates of ortho-phosphoric acid that are reacted formally singly and/or doubly with alcohols. Examples of suitable components (c) include the following:

(c1) largely water-insoluble polar esters of phosphoric acid from the group containing (c1.1) phosphoric triesters with monohydric alkanols having 5 to 22 carbon atoms, e.g., with n-, iso- or neopentanol, n-hexanol, n-octanol, 2-ethylhexanol, (c1.2) phosphoric triesters with diols or polyols, such as ethylene glycol, propylene glycol or glycerol, (c1.3) phosphoric triesters with aryl, alkylaryl, poly(alkyl) aryl and poly(arylalkyl)aryl alcohols, as for example with phenol, cresol, octylphenol, nonylphenol, triisobutylphenol, tri-n-butylphenol, tri(sec-butyl)phenol and/or tristyrylphenol (c1.4) phosphoric triesters with alkoxylated alcohols obtained by reacting the alcohol components specified above under (c1.1) to (c1.3) with alkylene oxides, preferably ($C_2$-$C_4$)alkylene oxides, and (c1.5) phosphoric triesters with alkoxylated alcohols obtained by reacting monohydric alkanols having 1 to 4 carbon atoms and alkylene oxides, preferably ($C_2$-$C_4$)alkylene oxides, or (c1.6) phosphoric triesters with a mixture of alcohols comprising two or more of the alcohol components specified above under groups (c1.1) to (c1.5), where the 3 alcohol components of the phosphoric ester from groups (c1.1) to (c1.5) may in each case be identical or different and are selected such that the ester can be used as a largely water-insoluble polar solvent.

Additionally suitable as component (c) are the following:

(c2) largely water-insoluble and at the same time polar phosphonates based on alkyl-, aryl-, alkylaryl-, poly (alkyl)-aryl- or poly(arylalkyl)-aryl-phosphonic acids doubly esterified with alcohols and/or with alkoxylated alcohols, preferably:

(c2.1) diesters of phosphonic acids with monohydric alkanols having 1 to 22 carbon atoms, e.g., with e.g., n-methanol, n-ethanol, n- or isopropanol, n-, iso- or t-butanol, n-, iso- or neo-pentanol, n-hexanol, n-octanol, 2-ethylhexanol, or else sec-butanol,
(c2.2) diesters of phosphonic acids with diols or polyols, such as ethylene glycol, propylene glycol or glycerol,
(c2.3) diesters of phosphonic acids with aryl, alkylaryl, poly(alkyl)aryl or poly(arylalkyl)aryl alcohols, as for example with phenol, cresol, octylphenol, nonylphenol, triisobutylphenol and/or tristyrylphenol,
(c2.4) diesters of phosphonic acids with alkoxylated alcohols which are obtained by reacting the alcohols specified above under (c2.1) to (c2.3) with alkylene oxides, preferably ($C_2$-$C_4$)alkylene oxides, or
(c2.5) diesters of phosphonic acids with a mixture of alcohols from two or more of the alcohol components specified above under groups (c2.1) to (c2.4),
where the 2 alcohol components of the phosphonic diester from groups (c2.1) to (c2.4) may in each case be identical or different and are selected such that the ester can be used as a largely water-insoluble polar solvent.

Among the alkyleneoxy units, preference is given to ($C_2$-$C_4$)alkylene oxide units, e.g., 1,2-ethyleneoxy, 1,2-propyleneoxy and/or butyleneoxy units (1,2-butyleneoxy, 2,3-butyleneoxy, and 2,2-dimethyl-1,2-ethyleneoxy units), more particularly 1,2-propyleneoxy and/or 1,2-ethyleneoxy units.

The alcohol components comprise preferably 1-200, more particularly 1-150, very particularly 1-100 alkyleneoxy units, preferably 1,2-ethyleneoxy units.

Preferred phosphoric esters (c1) (esters of ortho-phosphoric acid) are in particular, for example,
(c1.7) phosphoric triesters with alkoxylated short-chain alcohols having 1 to 22 carbon atoms in the alkyl radical and 1 to 30 alkyleneoxy units in the polyalkyleneoxy moiety, an example being tributoxyethyl phosphate (Clariant), more accurately or preferably tri[2-(n-butoxy)ethyl] phosphate,
(c1.8) phosphoric triesters with alkyl alcohols having 5 to 22 carbon atoms, examples being Hostaphat CG 120® (Clariant), tri-n-octyl phosphate ("TOF", Bayer), and,
(c1.9) phosphoric triesters based on ortho-phosphoric acid esterified partially with optionally alkoxylated alcohols having 1 to 22 carbon atoms in the alkyl radical or with optionally alkoxylated phenol derivatives, in each case having 0 to 30 alkyleneoxy units in the polyalkyleneoxy moiety, the remaining OH valences of the ortho-phosphoric acid having been subsequently alkoxylated (e.g., with 1 to 10 mol of alkylene oxide having 2 to 4 carbon atoms), as for example the reaction product of mono/dibutoxyethyl phosphate and 2 mol of ethylene oxide and/or 2 mol of propylene oxide (Clariant).

Preferred phosphonates (c2) (fully esterified phosphonic acids) are in particular, for example,
(c2.6) esters, reacted formally doubly with alcohols, of n-octylphosphonic acid, as for example the Hostarex Products® (Clariant).

In addition, the formulations of the invention may comprise further solvents, without losing the advantageous properties of the surfactant-solvent system. In connection with the present invention, examples of suitable additional solvents include apolar solvents, polar protic solvents or aprotic dipolar solvents, and mixtures thereof. Examples of solvents in the sense of the invention are
aliphatic or aromatic hydrocarbons, such as mineral oils, paraffins or toluene, xylenes and naphthalene derivatives, more particularly 1-methylnaphthalene, 2-methylnaphthalene, 6-16C aromatics mixtures such as, for example, the Solvesso® series (ESSO) with the products Solvesso® 100 (b.p. 162-177° C.), Solvesso® 150 (b.p. 187-207° C.), and Solvesso® 200 (b.p. 219-282° C.), and 6-20C aliphatics, which may be linear or cyclic, such as the products of the Shellsol® series, types T and K, or BP-n paraffins,
halogenated aliphatic or aromatic hydrocarbons such as methylene chloride or chlorobenzene,
esters such as triacetin (acetic triglyceride), butyrolactone, propylene carbonate, triethyl citrate, and ($C_1$-$C_{22}$)alkyl phthalates, especially ($C_4$-$C_8$)alkyl phthalates,
ethers such as diethyl ether, tetrahydrofuran (THF), dioxane, alkylene glycol monoalkyl and dialkyl ethers such as, for example, propylene glycol monomethyl ether, especially Dowanol® PM (propylene glycol monomethyl ether), propylene glycol monoethyl ether, ethylene glycol monomethyl ether or monoethyl ether, diglyme and tetraglyme,
amides such as dimethylformamide (DMF), dimethylacetamide, dimethylcaprylyl/capric fatty acid amide, and N-alkylpyrrolidones,
ketones such as the water-soluble acetone, but also water-immiscible ketones such as cyclohexanone or isophorone, for example,
nitriles such as acetonitrile, propionitrile, butyronitrile, and benzonitrile,
sulfoxides and sulfones such as dimethyl sulfoxide (DMSO) and sulfolane, and also
oils in general, examples being vegetable-based oils such as corn germ oil and rapeseed oil.

Frequently also suitable are combinations of different solvents which additionally comprise alcohols such as methanol, ethanol, n- and isopropanol, n-, iso-, t-, and 2-butanol.

Preferred additional organic solvents for the purposes of the present invention are more particularly amides such as dimethylcaprylyl/capric fatty acid amide and N-methylpyrrolidone.

With the surfactant/solvent systems of the invention comprising the components (b) and (c) that are used it is now possible, surprisingly, to produce stable oil dispersions of biscarbamate herbicides (desmedipham and/or phenmedipham), sulfonate herbicides (ethofumesate), and uracil herbicides (lenacil). Furthermore, the surfactant system of the invention favorably influences the pesticidal activity of the active ingredients incorporated.

The surfactant/solvent system (b) and (c) of the invention also allows the production of emulsifiable concentrates with active ingredients other than those recited here, provided they exhibit similar properties in terms of their solubilities. Also suitable, for example, are herbicides from the group of the phenoxyphenoxypropionates such as diclofop-methyl, cyhalofop-butynyl, the heteroaryloxyphenoxypropionates such as fenoxaprop-ethyl, fenoxaprop-P-ethyl, fluazifop-butyl, fluazifop-P-butyl, haloxyfop-methyl, haloxyfop-etotyl, haloxyfop-P-methyl, propquizofop, quizalofop-ethyl, quizalofop-P-ethyl or clodinafop-propargyl, from the group of the triazinones such as metamitron, metribuzin or hexazinone, from the group of the sulfonylureas such as triflusulfuron-methyl, amidosulfuron, iodosulfuron-methyl, tribenuron-methyl, triasulfuron, thifensulfuron-methyl, sulfosulfuron, sulfometuron-methyl, prosulfuron, primisulfuron-methyl, oxasulfuron, metsulfuron-methyl, ethoxysulfuron, ethametsulfuron-methyl, cyclosulfamuron, cinosulfuron, chlorsulfuron, chlorimuron-ethyl or bensulfuron-methyl, preferably in the form of the nonsalts, but also pyridylsulfonylureas of low water solubility, or other herbicides such as benfuresate, or other active ingredients such as the fungicide prochloraz and/or insecticides such as deltamethrin. This shows the flexibility of the surfactant/solvent system described. The compounds stated are known to the skilled worker from "The Pesticide Manual", British Crop Protection Council, 14$^{th}$ edition, 2006.

On dilution with water, the oil dispersions of the invention produce dispersions of oil phases in water or—with corresponding selection of the individual components—of aqueous phases in oil. Depending on composition, therefore, dispersions are obtainable that can be diluted either with water or with oil, with retention of the colloidal structure. Accordingly, the dispersions obtainable from the above-described concentrates via dilution are additionally provided by the invention.

The weight ratios of the combined active herbicidal ingredients of type (a), i.e., carbamate herbicides (a1) and/or (a2):ethofumesate (a3):lenacil (a4) may vary within wide limits, but generally are in the range from (1):(0.1):(0.01) to (1):(5):(3), preferably in the range from (1):(0.2):(0.05) to (1):(2):(2), more particularly in the range from (1):(0.5):(0.1) to (1):(1.5):(1).

The weight ratios of the combined active herbicidal ingredients in the four-way combination of the type (a1):(a2):(a3):(a4) are generally in the range from (1):(0.5):(0.2):(0.02) to (1):(10):(20):(10), preferably in the range from (1):(1):(0.5):(0.05) to (1):(6):(10):(5), more particularly in the range from (1):(1):(1):(0.3) to (1):(5):(8):(4).

The application rates of the herbicide components may vary within a wide range and are situated generally in the range of 100 and 5000 g of active substance per hectare (=AS/ha), preferably between 150 and 3500 g AS/ha, more particularly 200 and 2500 g AS/ha, very particularly 300 and 1200 g AS/ha for the total amount of herbicides (a1) to (a4).

The application rate of the individual herbicides here is generally in the range from:
10 to 500 g AS/ha, preferably 10 to 200 g AS/ha, more particularly 20 to 150 g AS/ha of desmedipham (a1),
15 to 1000 g AS/ha, preferably 15 to 500 g AS/ha, more particularly 20 to 200 g AS/ha of phenmedipham (a2),
15 to 1000 g AS/ha, preferably 20 to 500 g AS/ha, more particularly 20 to 250 g AS/ha of ethofumesate (a3),
5 to 500 g AS/ha, preferably 10 to 300 g AS/ha, more particularly 15 to 150 g AS/ha of lenacil (a4):

For identical herbicidal activity, the application rate in the case of the combined application of all four herbicides (a1)-(a4) is substantially below the application rates for the application of combinations or single applications of the biscarbamate herbicides of the type (a1) and (a2).

Consequently, particular interest attaches to stable formulations in which all four active ingredients are present, on the basis of their high biological activity—for an overall reduction in active ingredient content. Nevertheless, the optimum choice of weight ratios and of application rates is dependent on the development stage of the particular broadleaf or gramineous weeds, the prevailing weed spectrums, environmental factors, and climatic conditions, and so the weight ratios and application rates indicated above must be checked in each individual case.

The auxiliaries necessary for producing the stated formulations, such as, in particular, surfactants and solvents, are known in principle and are described, for example, in the following: McCutcheon's "Detergents and Emulsifiers Annual", MC Publ. Corp., Ridgewood N.J.; Sisley and Wood, "Encyclopedia of Surface active Agents", Chem. Publ. Co. Inc., N.Y. 1964; Schönfeldt, "Grenzflächenaktive Äthylenoxidaddukte", Wiss. Verlagsgesellschaft, Stuttgart 1976; Winnacker-Küchler, "Chemische Technologie", volume 7, C. Hanser-Verlag, Munich, 4$^{th}$ edition 1986.

Whereas the chemical "construction" of the individual components that can be employed is adequately described in such references, predictions concerning the properties of mixtures of such components for the formulation of a specific active ingredient system can generally not be inferred from the cited handbooks. When, for example, a surfactant/solvent combination is employed with which stable oil dispersions are produced for active ingredient combinations of desmedipham, phenmedipham, ethofumesate, and lenacil, at a relatively low "active ingredient loading", the products obtained when the active ingredient concentration is increased, in spite of the presence of surfactants, are no longer stable concentrates, but instead are unstable multiphase systems which also show a tendency toward severe crystallization of the active ingredients. This is a direct indicator of the importance of component (c) of the invention (ortho-phosphoric esters and/or phosphonic esters) as solvents for the stability of the oil dispersions to be produced. Generally speaking, the oil dispersions of the invention comprise the active ingredients (a1) to (a3) in dissolved form, whereas the active ingredient (a4) is present in suspended form.

The solvent (c) used, such as tributoxyethyl phosphate (TBEP), for example, therefore allows a higher loading of the formulation with the largely water-insoluble active ingredients (a1) to (a3) and hence surpasses other, structurally similar solvents such as tributyl phosphate (TBP) in terms of the "solvent power". Independently of this, however, in any given case, further solvents may also be necessary in order to obtain a stable oil dispersion which largely prevents crystallization of the active ingredients present.

Within the oil dispersions described, the active ingredient (a4) is present in a largely undissolved, i.e., suspended, form. Such dispersions of a solid in organic, surfactant-containing solvents frequently show a tendency on storage to form solid sediments which can no longer be shaken up. Growth in size of the dispersed crystals is another continually repeating problem in practice; as a consequence, after a spray liquor has been produced and subsequently applied by spraying, there may be instances of nozzle clogging.

It was therefore not an automatic expectation that the active ingredient (a4) could be integrated into the solution of the active ingredients (a1) to (a3) without such complications. Nevertheless, it was found that, in a product having the composition indicated in example 2, no sediment at all had formed after a standing time of one year. Nor had there been any change during this time in the average crystal size—of around 4 µm, for example—measured for (a4) directly after production.

Combinations of an ortho-phosphoric ester and/or a phosphonic ester as solvent and one or more surfactants comprising an aromatic-based surfactant, preferably a nonionic aromatic-based surfactant, are preferentially and especially suitable for producing stable oil dispersions.

A factor critical for the selection of further surfactant components is their acidity or basicity per unit weight or volume, which is expressed by the acid number or amine number. Too sharp an increase in the total acid number or amine number in the ready-to-use formulation is problematic insofar as it may entail flocculation/crystallization of the formulated active ingredient(s). When selecting further surfactant components, consequently, it is necessary to ensure that the total acid number or amine number does not increase too sharply. Preferably, therefore, besides nonionic surfactants, only acidic or basic components with a sufficiently low acid or amine number are suitable. Since this number correlates, in turn, with the molecular weight, further surfactant components contemplated are in many cases also acidic or basic derivatives of compounds having a high molecular weight, such as tristyrylphenol alkoxylates, for example. In the case of nonionic surfactants, these considerations are irrelevant, in accordance with the nonionic nature of these components.

In this context it should additionally be noted that the surfactant/solvent systems described permit the production of stable oil dispersions having an active ingredient loading and composition that is variable within wide limits: accordingly, for example, the active ingredient loading can vary between 20 and 40, preferably between 24 and 30, percent by weight. Preferred weight ratios of the ortho-phosphoric ester/phosphonic ester:aromatic-based surfactant components, depending on active ingredient loading and composition of the emulsifiable concentrates, are 100:1 to 1:100, more preferably 20:1 to 1:20, more preferably still 5:1 to 1:5.

Concentrated oil dispersions produced in accordance with the present invention comprise a priori no additional water, but only the residual water present in the stated commercially available surfactants and surfactant mixtures, polymers, and solvents. Owing to the surfactants present in the formulations, however, it is possible to dilute the stated formulations with water as far as a critical volume fraction, without this resulting in any clouding or destabilization of the formulation. The products in this case are, formally, first W/O microemulsions, which on further increase in the water fraction undergo transition to W/O emulsions and lastly—on further dilution with water—to O/W emulsions. In addition to the surfactant/solvent mixture (b)+(c) of the invention, therefore, the invention also encompasses liquid formulations of the active ingredients of type (a1), (a2), (a3), and (a4) that comprise (additional) water.

With the aid of the component mixtures (b)+(c) it is possible to produce preferably concentrated liquid oil dispersions comprising
(a) 1 to 50%, preferably 10 to 40%, by weight of active ingredients (a1) to (a4),
(b) 3 to 70%, preferably 5 to 60%, by weight of surfactants,
(c) 5 to 70%, preferably 10 to 50%, by weight phosphoric esters or phosphonic esters (c1) and/or (c2),
(d) 0 to 40%, preferably 0 to 20%, by weight of further solvents,
(e) 0 to 20%, preferably 0 to 10%, by weight of further, customary formulating auxiliaries,
(f) 0 to 20%, preferably 0 to 10%, by weight of water.

Largely water-free concentrated oil dispersions represent an advantageous application form of the active herbicidal ingredients of type (a) and are preferably provided by the invention. Particular preference is given to oil dispersions which comprise
(a) 10 to 40%, preferably 15 to 30%, by weight of active ingredients (a1) to (a4),
(b) 5 to 70%, preferably 15 to 60%, by weight of surfactants,
(c) 10 to 70%, preferably 15 to 50%, by weight of phosphoric esters or phosphonic esters (c1) and/or (c2),
(d) 0 to 40%, preferably 0 to 20%, by weight of further solvents, and
(e) 0 to 20%, preferably 0 to 10%, by weight of further, customary formulating auxiliaries.

Examples of typical formulating auxiliaries e) include agents which influence the thixotropy and rheology of the oil dispersions, examples being thickeners, frost preventatives, evaporation inhibitors, preservatives, odorants, colorants, defoamers, fillers, carriers, and dyes, pH modifiers (buffers, acids, and bases), and others.

Preferred formulating auxiliaries e) are
thickeners, in an amount of 0.001 to 5% by weight, for example,
frost preventatives and evaporation inhibitors such as glycerol, in an amount of 2 to 10% by weight, for example, and
preservatives, e.g., Mergal K9N® (Riedel) or Cobate C®, in the customary use concentrations for the particular agents employed in each case.

Thickeners contemplated, generally speaking, are all thickeners that are suitable or used for crop protection compositions, examples being inorganic (mineral) thickeners such as aluminum silicate-based thickeners or thickeners of another type, such as organic thickeners, examples being agar agar, carrageen, tragacanth, gum arabic, alginates, pectins, polyose, guar flour, carob kernel flour, starch, dextrins, cellulose ethers such as carboxymethylcellulose and hydroxyethylcellulose, polyacrylic and polymethacrylic compounds, vinyl polymers, polyethers or polyamides.

Thickeners contemplated include aluminum silicate-based thickeners, examples being those such as hectorites, montmorillonites, saponites, kaolinites, bentonites, attapulgites, etc. Examples of thickeners of these kinds are the Attagels® from Engelhardt Corp., e.g., Attagel 50, a magnesium aluminum hydrosilicate (attapulgite), or the ®Bentone series from Elementis such as ®Bentone EW, a magnesium aluminum hydrosilicate (bentonite), or other silica derivatives (e.g., ®Bentone 38, a phyllosilicate based on an organically modified smectite).

Also contemplated are organic thickeners. Examples of preferred organic thickeners are xanthans (heteropolysaccharides) such as the Rhodopol® products from Rhodia, e.g., Rhodopol 50 MC (xanthan gum) or Rhodopol 23 (a xanthan heteropolysaccharide).

The thickeners can also be used in combination. In this context, combinations of organic and mineral thickeners may be among those which are appropriate.

The appropriate fraction of thickeners is dependent on the viscosity of the formulation and on the individual thickeners and generally speaking is, for example, 0.001% to 10% by weight, preferably 0.005% to 5% by weight, based on the weight of the formulation. The fraction of aluminum silicate-based thickeners in the oil dispersions of the invention is preferably 0.01% to 5% by weight, more preferably 0.1% to 3.5% by weight. In the case of xanthan-type thickeners the fraction is preferably 0.001% to 5% by weight, more particularly 0.005% to 1% by weight.

The formulations and spray liquors produced with the surfactant/solvent system of the invention feature results in application which are advantageous from the biological standpoint too. Hence it is observed that the biological activity of the active ingredients (a1) to (a4) used in the formulations of the invention is boosted, in some cases synergistically.

The formulations permit effective control of a sizable number of economically important weeds. These include typical monocotyledonous and dicotyledonous weeds which occur in beet crops, examples being weeds of the following species: *Aethusa cynapium, Amaranthus retroflexus, Atriplex patula, Brassica sp., Capsella bursa pastoris, Chenopodium album, Echinocloa crus-galli, Fumaria officinalis, Galinsoga parviflora, Galium aparine, Lamium amplexicaule, Lamium purpureum, Matricaria chamomilla, Mercurialis annua, Myosotis arvensis, Poa annua, Polygonum aviculare, Polygonum convolvulus, Polygonum lapathifolium, Polygonum persicaria, Sinapis arvensis, Solanum nigrum, Sonchus arvensis, Stellaria media, Thlaspi arvense,*

Urtica urens, Veronica arvensis, Veronica hederifolia, Veronica persica and Viola arvensis.

In Examples A) and B) below, quantities are given by weight, unless indicated otherwise.

A) PREPARATION EXAMPLES

Table 1 reports the compositions for oil dispersion concentrates (Preparation Examples F1 to F11). The oil dispersion concentrates, each readily dispersible in water, were obtained by mixing the components with heating and, after the mixture had cooled, grinding it in a ball mill with agitator mechanism to a particle size of on average about 4 µm.

TABLE 1

Stable oil dispersions

Example (#)/fractions of the components in % by weight

| Comp. | F1 | F2 | F3 | F4 | F5 | F6 | F7 | F8 | F9 | F10 | F11 |
|---|---|---|---|---|---|---|---|---|---|---|---|
| (a1) | 4.7 | 4.3 | 4.3 | 3.0 | 3.0 | 3.0 | 3.0 | 6.7 | 6.7 | 3.0 | 3.0 |
| (a2) | 6.0 | 5.5 | 5.5 | 5.5 | 5.5 | 6.7 | 6.7 | 3.0 | 3.0 | 4.3 | 4.3 |
| (a3) | 7.5 | 6.9 | 6.9 | 8.0 | 8.0 | 6.7 | 6.7 | 6.7 | 6.7 | 9.2 | 9.2 |
| (a4) | 2.7 | 4.9 | 2.5 | 2.5 | 4.9 | 2.5 | 4.9 | 2.5 | 4.9 | 2.5 | 4.9 |
| (b1-1) | 19.4 | 19.4 | 19.4 | 19.4 | 19.4 | 19.4 | 19.4 | 19.4 | 19.4 | 19.4 | 19.4 |
| (b1-2) | 4.3 | 4.3 | 4.3 | 4.3 | 4.3 | 4.3 | 4.3 | 4.3 | 4.3 | 4.3 | 4.3 |
| (b2-1) | 21.6 | 21.6 | 21.6 | 21.6 | 21.6 | 21.6 | 21.6 | 21.6 | 21.6 | 21.6 | 21.6 |
| (b2-2) | 2.1 | 2.1 | 2.1 | 2.1 | 2.1 | 2.1 | 2.1 | 2.1 | 2.1 | 2.1 | 2.1 |
| (c1-1) | 30.7 | 30.0 | 32.4 | 32.6 | 30.2 | 32.7 | 30.3 | 32.7 | 30.3 | 32.6 | 30.2 |
| (e-1) | 1.0 | 1.0 | 1.0 | 1.0 | 1.0 | 1.0 | 1.0 | 1.0 | 1.0 | 1.0 | 1.0 |

Abbreviations for Table 1:
Comp.=component
(a1)=desmedipham
(a2)=phenmedipham
(a3)=ethofumesate
(a4)=lenacil
(b1-1)=ethoxylated tri(sec-butyl)phenol with 6 EO units, nonionic surfactant
(b1-2)=phosphated phenol ethoxylate with 4 EO units, free acid, anionic surfactant
(b2-1)=ethoxylated castor oil with 40 EO units, nonionic surfactant
(b2-2)=phosphated ethoxylated isotridecyl alcohol with 20 EO units, anionic surfactant
(c1-1)=tri(butoxyethyl) phosphate
(e-1)=thickener, silica derivative (phyllosilicate based on an organically modified smectite)

Example F12: Comparative Example (EC Formulation)

A formulation according to Example 1 was produced as an emulsifiable concentrate without the lenacil herbicide component. The fractions of the components in the emulsifiable concentrate were 4.7% by weight (a1), 6.0% by weight (a2), 7.5% by weight (a3), 19.4% by weight (b1-1), 4.3% by weight (b1-2), 21.6% by weight (b2-1), 2.1% by weight (b2-2), and 31.7% by weight (c1-1). The abbreviations (a1) to (c1-1) used have the same definitions as elucidated for Examples F1 to F11.

The Comparative Example (Example F12) is used in the Biological Examples.

B) BIOLOGICAL EXAMPLES

1. Preparation of Spray Liquors

A water application rate of 300 l/ha was introduced as an initial charge. Subsequently, the herbicides were added with stirring, in accordance with the application rates and types specified in Tables 2 and 3 (see later on below), to form a homogeneous spray liquor. In tank mixes, lenacil was used in the form of a standard formulation (Venzar®, DuPont, an 80 percent, water-dispersible powder).

2. Biological Trials

The abbreviations used below have the following meanings:
a.i.=active ingredient (based on 100% active substance), synonymous with AS=active substance
g a.i./ha=gram of active ingredient per hectare
F(#)=Preparation Example F(#) from section A)
Venzar=®Venzar (lenacil straight, WP80, DuPont)
l/ha=liter/hectare
PMP=phenmedipham
DMP=desmedipham
ETH=ethofumesate
LEN=lenacil
BEAVA=*Beta vulgaris* (sugar beet)
BRSNW=*Brassica napus*
POAAN=*Poa annua*
MATCH=*Matricaria chamomilla*
AMARE=*Amaranthus retroflexus*
STEME=*Stellaria media*
CHEAL=*Chenopodium album*
GALAP=*Galium aparine*

Plant seeds were sown to a depth of 1 cm and grown in a chamber with a controlled climate (12 h light, temperature: day 18° C., night 11° C.) to a growth stage of BBCH 10 to BBCH 11. The plants were treated with spray liquors of the herbicides on a laboratory spray track. The water application rate for spray application was 300 l/ha. Following treatment, the plants were replaced in the controlled-climate chamber.

2.1 Combinations of (a1) to (a3) PMP/DMP/ETH with (a4) LEN 21 days after application, the maximum damage to BEAVA was achieved and was evaluated; the activity against the broadleaf weeds was determined 14 days after spraying. The herbicidal activity was evaluated on a scale from 0 to 100%: 0%=no detectable activity in comparison to untreated plants; 100%=all of the plants killed.

The evaluations produced the results given in Tables 2 and 3, which clearly show the synergistic effect of lenacil on the PMP/DMP/ETH active ingredient combination when the four active ingredients are formulated in accordance with Example 1 from Table 1. Moreover, the joint formulation of the four active ingredients according to Example F1 from Table 1 leads to significantly less damage than the external admixing of lenacil in a tank mix to the EC formulation according to the comparative example (section A, Preparation Example F12).

TABLE 2

| Experiment/ product | Dose [g a.i./ha] | | | | Damaged BEAVA [%] | Activity against weeds* [%] |
|---|---|---|---|---|---|---|
| | PMP | DMP | ETH | LEN | | |
| untreated | | | | | 0 | 0 |
| Venzar | | | | 81 | 0 | 0 |
| F12 | 180 | 141 | 225 | | 10 | 87 |
| F12 + Venzar | 180 | 141 | 225 | 81 | 25 | 85 |
| F1 | 180 | 141 | 225 | 81 | 10 | 91 |

*average from BRSNW, POAAN, MATCH, AMARE, STEME, CHEAL, GALAP

TABLE 3

| Experiment/ product | Dose [g a.i./ha] | | | | Damaged BEAVA [%] | Activity against BRSNW [%] | Activity against AMARE [%] | Activity against STEME [%] |
|---|---|---|---|---|---|---|---|---|
| | PMP | DMP | ETH | LEN | | | | |
| untreated | | | | | 0 | 0 | 0 | 0 |
| Venzar | | | | 27 | 0 | 0 | 0 | 0 |
| F12 | 60 | 47 | 75 | | 0 | 50 | 96 | 84 |
| F12 + Venzar | 60 | 47 | 75 | 27 | 10 | 45 | 96 | 73 |
| Example F1 | 60 | 47 | 75 | 27 | 0 | 63 | 99 | 93 |

2.2 Comparative Trials with Combinations of (a1) to (a3) PMP/DMP/ETH and (a4) LEN In further trials under glass, the formulations from section A (Preparation Examples F1 and F12) were mixed alone or in combination with Venzar in a tank mix method into water, and were tested by the postemergence method against a number of weeds as well as for damage to sugar beet at growth stage 10 to 11 in each case. The herbicidal activity was evaluated as in section B) Example 2.1. The results are compiled in Tables 4 to 10.

TABLE 4

Synergistic herbicidal postemergence effect

| Trial/ formulation | Active ingredients/ application rate [a.i./ha] | Effect [%] on AMARE | Effect [%] on STEME |
|---|---|---|---|
| F1 | 47 g (a1) + 60 g (a2) + 75 g (a3) + 27 g (a4) (Ready-mix) | 95 | 93 |
| Venzar | 27 g (a4) (lenacil straight) | 0 | 0 |
| F12 | 47 g (a1) + 60 g (a2) + 75 g (a3) (ready-mix) | 75 | 84 |

Note for Table 4:
Evaluation took place 21 days after application

TABLE 5

Synergistic herbicidal postemergence effect

| Trial/ formulation | Active ingredients/ application rate [a.i./ha] | Effect [%] on BRSNW |
|---|---|---|
| F1 | 94 g (a1) + 120 g (a2) + 150 g (a3) + 54 g (a4) (ready-mix) | 80 |
| Venzar | 54 g (a4) (lenacil straight) | 0 |
| F12 | 94 g (a1) + 120 g (a2) + 150 g (a3) (ready-mix) | 63 |

Note for Table 5:
Evaluation took place 10 days after application

TABLE 6

Synergistic herbicidal postemergence effect

| Trial/ formulation | Active ingredients/ application rate [a.i./ha] | Effect [%] on BRSNW | MATCH | CHEAL |
|---|---|---|---|---|
| F1 | 141 g (a1) + 180 g (a2) + 225 g (a3) + 81 g (a4) (ready-mix) | 92 | 100 | 88 |
| Venzar | 81 g (a4) (lenacil straight) | 0 | 0 | 0 |
| F12 | 141 g (a1) + 180 g (a2) + 225 g (a3) (ready-mix) | 68 | 70 | 75 |

Note for Table 6:
Evaluation took place 21 days after application

TABLE 7

Herbicidal postemergence activity and selectivity

| Trial/ formulation | Active ingredients/ application rate [a.i./ha] | Harmful effect [%] on BEAVA | Herbicidal effect [%] on AMARE |
|---|---|---|---|
| F1 | 47 g (a1) + 60 g (a2) + 75 g (a3) + 27 g (a4) (ready-mix) | 0 | 95 |
| F12 + Venzar | Tank mix of 47 g (a1) + 60 g (a2) + 75 g (a3) (ready-mix) + 27 g (a4) (lenacil straight) | 10 | 65 |

Note for Table 7:
Evaluation took place 21 days after application

TABLE 8

Herbicidal postemergence activity

| Trial/ formulation | Active ingredients/ application rate [a.i./ha] | Herbicidal effect [%] on POLCO | Herbicidal effect [%] on STEME |
|---|---|---|---|
| F1 | 47 g (a1) + 60 g (a2) + 75 g (a3) + 27 g (a4) (ready-mix) | 90 | 93 |
| F12 + Venzar | Tank mix of 47 g (a1) + 60 g (a2) + 75 g (a3) (ready-mix) + 27 g (a4) (lenacil straight) | 81 | 73 |

Note for Table 8:
Evaluation took place 10 days after application

TABLE 9

Herbicidal postemergence effect

| Trial/ formulation | Active ingredients/ application rate [a.i./ha] | Herbicidal effect [%] on BRSNW | POAAN | GALAP |
|---|---|---|---|---|
| F1 | 94 g (a1) + 120 g (a2) + 150 g (a3) + 54 g (a4) (ready-mix) | 80 | 60 | 85 |
| F12 + Venzar | Tank mix of 94 g (a1) + 120 g (a2) + 150 g (a3) (ready-mix) + 54 g (a4) (lenacil straight) | 63 | 33 | 75 |

Note for Table 9:
Evaluation took place 10 days after application

TABLE 10

Improvement in selectivity postemergence

| Trial/ formulation (a1) + (a2) + (a3) + (a4) | Active ingredients | Harmful effect [%] on BEAVA at application rate of [g a.i./ha] | | | | |
|---|---|---|---|---|---|---|
| | | 91 + 14 | 182 + 27 | 364 + 54 | 546 + 81 | 728 + 108 |
| F1 | (a1) + (a2) + (a3) + (a4) (ready-mix) | 0 | 0 | 5 | 10 | 15 |
| F12 + Venzar | Tank mix: (a1) + (a2) + (a3) (ready-mix) + (a4) (lenacil straight) | 5 | 10 | 15 | 25 | 30 |

Note for Table 10:
Evaluation was made 21 days after application

The invention claimed is:

1. An oil dispersion comprising:
   (a) a herbicidally effective amount of a plurality of compounds comprising:
       desmedipham of the formula (a1):

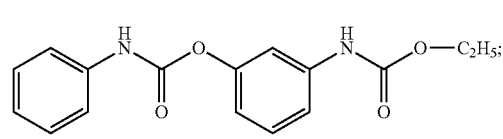

(a1)

phenmedipham of the formula (a2):

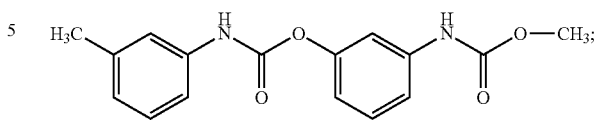

(a2)

ethofumesate of the formula (a3):

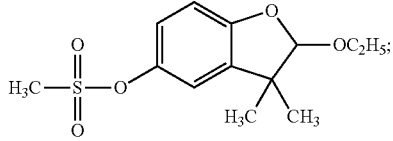

(a3)

and lenacil of the formula (a4):

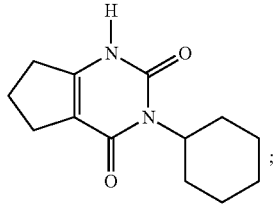

(a4)

(b) one or more surfactants;
   (c) one or more compounds, selected from the group consisting of fully esterified organic phosphates and fully esterified phosphonates, as solvents;
   (d) if desired, other organic solvents;
   (e) if desired, other, customary formulating auxiliaries; and
   (f) if desired, water
   wherein the amounts of components (a) to (f) are:
   (a) 15% to 30% by weight of active ingredients (a1) to (a4),
   (b) 15% to 60% by weight of surfactants,
   (c) 15% to 50% by weight of phosphoric triesters or phosphonic diesters,
   (d) 0% to 20% by weight of further solvents, (e) 0% to 10% by weight of further, customary formulating auxiliaries,
(f) 0% to 10% by weight of water,
wherein the weight ratio of active ingredients (a1):(a2):(a3):(a4) is in a range of from (1):(1):(1):(0.3) to (1):(5):(8):(4).

2. The oil dispersion as claimed in claim 1 wherein the one or more surfactants (b) is (b1) a carbocyclic aromatics based surfactant, (b2) a non-aromatic based surfactant that contains no carbocyclic aromatic moieties, or a mixture of (b1) and (b2).

3. The oil dispersion as claimed in claim 1;
wherein the one or more surfactants (b) is (b1) a carbocyclic aromatics based surfactant selected from the group consisting of:
(b 1.1) phenols, phenyl (CcC4)alkyl ethers or (poly)alkoxylated phenols;
(b 1.2) (poly)alkylphenols or (poly)alkylphenol alkoxylates;
(b 1.3) polyarylphenols or polyarylphenol alkoxylates;
(b 1.4) compounds which formally represent the reaction products of the molecules described under (b1.1) to (b1.3) with sulfuric acid or phosphoric acid, and their salts neutralized with suitable bases; and
(b1.5) acidic (poly)alkyl- and (poly)aryl-benzenesulfonates and such neutralized with suitable bases.

4. The oil dispersion as claimed in claim 1;
wherein the one or more surfactants (b) is (b1) a carbocyclic aromatics based surfactant selected from the group consisting of:
phenol reacted with 4 to 10 mol of ethylene oxide;
triisobutylphenol, tri(sec-butyl)phenol or tri(n-butyl)phenol reacted with 4 to 50 mol of ethylene oxide;
nonylphenol reacted with 4 to 50 mol of ethylene oxide;
tristyrylphenol reacted with 4 to 150 mol of ethylene oxide; and
acidic (linear) dodecylbenzenesulfonate.

5. The oil dispersion as claimed in claim 1;
wherein component (c) comprises one or more compounds selected from the group consisting of (c1) and (c2):
(c1) water-insoluble polar esters of phosphoric acid from the group consisting of:
(c1.1) phosphoric triesters with monohydric alkanols having 5 to 22 carbon atoms;
(c1.2) phosphoric triesters with dials or polyols;
(c1.3) phosphoric triesters with aryl, alkylaryl, poly(alkyl)aryl and poly(arylalkyl)aryl alcohols;
(c1.4) phosphoric triesters with alkoxylated alcohols obtained by reacting the alcohol components specified above under (c1.1) to (c1.3) with alkylene oxides;
(c1.5) phosphoric triesters with alkoxylated alcohols obtained by reacting monohydric alkanols having 1 to 4 carbon atoms and alkylene oxides; and
(c1.6) phosphoric triesters with a mixture of alcohols comprising two or more of the alcohol components specified above under groups (c1.1) to (c1.5);
where the 3 alcohol components of the phosphoric ester from groups (c1.1) to (c1.5) may in each case be identical or different and are selected such that the ester can be used as a water-insoluble polar solvent; and
(c2) water-insoluble and at the same time polar phosphonates based on alkyl-, aryl-, alkylaryl-, poly(alkyl)-aryl-, or poly(arylalkyl)-aryl-phosphonic acids doubly esterified with alcohols and/or with alkoxylated alcohols, selected from the following group:
(c2.1) diesters of phosphonic acids with monohydric alkanols having 1 to 22 carbon atoms;
(c2.2) diesters of phosphonic acids with diols or polyols;
(c2.3) diesters of phosphonic acids with aryl, alkylaryl, poly(alkyl)aryl or poly(arylalkyl)aryl alcohols;
(c2.4) diesters of phosphonic acids with alkoxylated alcohols which are obtained by reacting the alcohols specified above under (c2.1) to (c2.3) with alkylene oxides; and
(c2.5) diesters of phosphonic acids with a mixture of alcohols from two or more of the alcohol components specified above under groups (c2.1) to (c2.4);
where the 2 alcohol components of the phosphonic diester from groups (c2.1) to (c2.4) may in each case be identical or different and are selected such that the ester can be used as a largely water-insoluble polar solvent.

6. The oil dispersion as claimed in claim 1;
wherein component (c) is selected from the group consisting of:
(c1.7) phosphoric triesters with alkoxylated short-chain alcohols having 1 to 22 carbon atoms in the alkyl radical and 1 to 30 alkyleneoxy units in the polyalkyleneoxy moiety;
(c1.8) phosphoric triesters with alkyl alcohols having 5 to 22 carbon atoms; and
(c1.9) phosphoric triesters based on ortho-phosphoric acid esterified partially with optionally alkoxylated alcohols having 1 to 22 carbon atoms in the alkyl radical or with optionally alkoxylated phenol derivatives, in each case having 0 to 30 alkyleneoxy units in the polyalkyleneoxy moiety, the remaining OH valences of the ortho-phosphoric acid having been subsequently alkoxylated.

7. The oil dispersion as claimed in claim 1;
wherein component (c) is tributoxyethyl phosphate.

8. The oil dispersion as claimed in claim 1,
wherein the combination of compounds (a1), (a2), (a3), and (a4) has a synergistic effect that gives a greater herbicidal activity than if the compound (a4) is applied separately from the herbicides (a1), (a2), and (a3).

9. A method of controlling unwanted plant growth, comprising: applying an effective amount of the oil dispersion as claimed in claim 1, optionally following dilution with water, to the plants, plant parts or cultivation area.

10. A process for preparing the oil dispersion as defined in claim 1, comprising: mixing the components (a) to (f) with one another.

11. The method as claimed in claim 10; wherein weed plants are controlled selectively in beet crops.

* * * * *